United States Patent [19]  [11] 3,954,726
Fiecchi  [45] May 4, 1976

[54] DOUBLE SALTS OF S-ADENOSIL-L-METHIONINE

[75] Inventor: Alberto Fiecchi, Milan, Italy

[73] Assignee: Bioresearch Limited, Milan, Italy

[22] Filed: June 24, 1974

[21] Appl. No.: 482,153

[30] Foreign Application Priority Data
June 27, 1973 Italy .................................. 25895/73
May 24, 1974 Italy .................................. 23148/74

[52] U.S. Cl. ........................ 260/211.5 R; 195/28 N; 424/180; 424/181
[51] Int. Cl.² ........................................ C07H 19/16
[58] Field of Search ............................. 260/211.5 R

[56] References Cited
UNITED STATES PATENTS
3,642,772  2/1972  Haid et al. .................... 260/211.5 R
3,707,536  12/1972 Haid et al. .................... 260/211.5 R Primary Examiner—Johnnie R. Brown
Attorney, Agent, or Firm—Stevens, Davis, Miller & Mosher

[57] ABSTRACT

New double salts extremely stable of S-Adenosil-L-methionine with sulphuric acid and p.toluensulphonic acid of the formula $SAM^+.HSO_4^-.H_2SO_4.2CH_3C_6H_4SO_3H$ and $SAM^+.HSO_4^-.H_2SO_4.CH_3C_6H_4SO_3H$, process for the preparation thereof and therapeutic compositions containing them.

13 Claims, No Drawings

DOUBLE SALTS OF S-ADENOSIL-L-METHIONINE

This invention relates to new enzymatic salts, a process for their preparation and the therapeutic compositions which contain them.

More precisely this invention relates to new extremely stable salts of S-Adenosil-L-Methionine (SAM), to a process which enables it to be prepared simply and economically on an industrial scale and to new pharmaceutical compositions which contain them as the active principle, for use in numerous fields of human therapy.

SAM is notably a product of natural origin, found in all living organisms from bacteria to plants, from single cell organisms to superior mammals including man, the structure of which has been known for some time and is identified by the following formula:

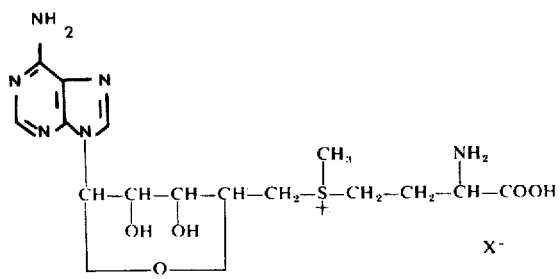

in which X is a generic anion.

In living organisms SAM is formed by the intervention of enzymes (S-adenosilmethioninsynthetasis or S-adenosiltransferasis) in the cytoplasmatic ambit starting from methionine assumed with the nutriments or from ATP present as energy reserve in every living cell.

It has also been known for some time that SAM is a product of fundamental importance in a large number of biological reactions of enzymatic transmethylation, because of which it has always been considered a very important reagent in biochemistry. The big problem with this substance has however always been its extreme instability at ambient or above ambient temperatures, and its methods of production which are laborious and cannot easily be carried out on an industrial scale.

In recent years, research directed towards stabilising SAM to such an extent as to make it possible to use it in the field of biological research has been directed towards the preparation of salts which are stable under normal temperature and humidity conditions.

In this way the chloride and sulphate of SAM have been produced, but they are of use only as reagents in biochemistry for short times, because even in the dry state their stability is limited in time at low temperatures. Furthermore their preparation processes are useful for the production of small quantities, but certainly not for production on an industrial scale.

We have now completely unexpectedly found new salts of SAM which are indefinitely stable with time at temperatures up to 45°C, and which can be prepared by a new process easily carried out economically on an industrial scale, giving high yields. These salts have proved surprisingly to possess strong curative power in many fields of human therapy, often apparently without correlation between them.

The new salts according to the present invention are double salts of SAM with p-toluenesulphonic acid and sulphuric acid, corresponding to the formula $SAM^+.HSO_4^-.H_2SO_4.2CH_3C_6H_4SO_3H$, and $SAM^+.HSO_4^-.H_2SO_4.CH_3C_6H_4SO_3H$ respectively.

The great technical progress achieved by these new salts can be seen from the following table which compares the stability with time, at 45°C, in the dry state, of the two most stable salts of SAM known up to the present time, i.e. the chloride and sulphate, with the new di-sulphate, di-p.toluenesulphonate. The figures refer to the percentage of SAM residue after the times indicated:

TABLE 1

| Anion | 30 d | 60 d | 120 d | 180 d |
|---|---|---|---|---|
| Chloride | 20 | — | — | — |
| Sulphate | 50 | 5 | — | — |
| Di-sulphate di-p. toluensulphonate | 100.1 | 99.9 | 100.2 | 100.4 |

The stability values obtained with the di-sulphate mono-p.toluenesulphonate are completely equivalent to those reported for the di-sulphate di-p.toluenesulphonate.

The process for preparing the new salts according to the invention comprises essentially the following stages:

a. preparation of a solution rich in SAM either by extraction from natural substances which contain it or by enzymatic synthesis from adenosin triphosphate (ATP) and methionine b. precipitation of the SAM present in the filtered aqueous solution by a saturated aqueous solution of picrolonic acid or by solutions of the same acid in organic solvents soluble in water such as methyl, ethyl, propyl, isopropyl, n-butyl, or iso-butyl alcohols; or acetone, methylethylketone, methylisobutylketone, ethyl acetate, tetrahydrofuran, 2-methoxyethanol, 2-ethoxyethanol, dioxan or dimethylformamide.

c. dissolving the filtered precipitate in a mixture consisting of equal parts by volume of a solvent partially miscible with water such as methylethylketone, methylisobutylketone, n-butanol or isobutanol and a solution of equal normality of p-toluensulphonic acid and sulphuric acid.

d. separation of the organic layer and addition to the aqueous solution of an organic ketone or alcohol solvent completely soluble in water.

e. redissolving the precipitate in a 10–20% solution of n-toluenesulphonic acid in methanol and treating the solution with decolouring charcoal.

f. addition to the concentrate of an organic solvent able to precipitate the pure SAM in a well crystalline and easily filterable form.

As stated, stage (a) of the process can be carried out in different ways which are equally efficient for the purposes of obtaining a concentrated solution of SAM.

According to one alternative yeast (Saccharomyces Cerevisiae, Torulopsis utilis, Candida utilis etc.), enriched in SAM by the addition of methionine under suitable conditions (Schlenk, Enzymologia 29, 283 (1965)), with ethyl acetate and then with sulphuric acid having a normality between 0.1 and 0.5, preferably 0.35 N. at ambient temperature, so as to cause the lysis of the cells and the passage into solution of practically 100% of the SAM present.

Preferably quantities of water and acetate between 1/20 and 1/5 of the weight of the humid cells are used, and the treatment is protracted for a time between 15 and 45 minutes, preferably for 30 minutes.

Sulphuric acid is then added, and lysis is carried out for a time between 1 hour and 2 hours, preferably 1 hour and a half.

It should be noted that the lysis of the yeast cells conducted with a mixture of organic solvent and dilute sulphuric acid is much more convenient than that normally carried out with perchloric acid at ambient temperature, or with formic acid or acetic acid at 60°C and the like, in that not only does it take place at ambient temperature, which is very favourable to the stability of the SAM, but is conducted under such conditions that the solution can be easily filtered from the cellular residues, and does not contain any of the impurities which are present when the other lysant means are used, and which are difficult to eliminate with the known processes for preparing pure SAM.

According to a further alternative, the stage (a) of preparing the SAM for enzymatic synthesis is carried out by the action of the enzyme ATP-methionine-adenosiltransferasis (E.C. 2.4.2.12) on an incubation mixture containing adenosiltriphosphate (ATP) and methionine.

The essential condition for the purposes of the industrial execution of this method is that the enzyme is pure and is in a form which is easily isolated both from the initial incubation mixture and from the SAM produced.

The applicant has discovered a process for purifying the enzyme ATP-methionine-adenosiltransferasis by chromatography by affinity, plus a column reaction method, which enable the aforesaid objects to be attained.

The affinity chromatography of the specific enzyme according to the present invention is carried out by percolating a solution containing it, for example a raw extract of yeast or "Escherichia coli", through a column filled with a support solid to which a group has been covalently bonded which acts as a competitive inhibiter of the enzyme itself.

It has been surprisingly found that an excellent filling for such a purification column consists of an activated gel of polysaccharides to which L-lysine has been covalently bonded. The affinity of the specific enzyme for the lysine residue bonded to the solid matrix causes a delay in elution of the enzyme by the column, and it is thus possible to obtain separation from the other proteins in a very pure form.

However the separation of the enzyme from the eluate which contains it, for use in the next enzymatic synthesis stage, has given completely unsatisfactory results because once separated, its stability diminished with time, and in addition after being used only once in the synthesis of the SAM, it was destroyed in the subsequent SAM isolation operations.

The applicant has found that excellent results are obtained instead by absorbing the eluate containing the specific enzyme in a suitable support solid and carrying out the catalytic reaction between methionine and ATP in the column, leading to the formation of SAM.

A suitable support solid consists of a polysaccharide activated by a reagent suitable for bonding proteins to solid supports, such as cyanogen bromide.

By percolating a solution of ATP and methionine in a suitable buffer solution through the column, an eluate is obtained at the base of the column containing the SAM.

The stage (b) of the process enables the SAM to be separated in a state of high purity. In fact, in an acid environment the only compound precipitated by picrolonic acid in SAM, as is shown by thin layer chromatography in accordance with Anal. Biochem. 4, 16–28 (1971).

Picrolonic acid has thus an extremely and surprisingly selective action.

The other precipitating agents added up to the present, such as picric acid, Reinecke salt, or boric acid, give very impure precipitates which always require a subsequent purification of the SAM by ion exchange column chromatography, a process which is extremely costly and difficult to carry out industrially. It is also difficult to obtain the product with the necessary purity. The use of aqueous solutions of picrolonic acid or solutions of the same acid in the aforementioned organic solvents does not present particular problems, and is an operation which is carried out at ambient temperature.

The stage (c) is preferably carried out with solutions containing p-toluenesulphonic acid and sulphuric acid in concentrations both between 0.05 and 0.2 N, preferably 0.1 N, and with an organic solvent particularly miscible with water such as methylethylketone or n-butanol. The use of the organic solvent enables the aqueous acid solutions to be very much reduced and practically eliminates all the picrolonic acid.

The stage (d) of the process is carried out by preferably using between 4 and 8 volumes (with respect to the volume of the aqueous solution) of a solvent chosen from the group comprising acetone, methyl alcohol, ethyl alcohol and propyl alcohol.

It has also been surprisingly found that if in stage (e) the minimum quantity of methanol necessary to dissolve the precipitate originating from stage (d) is used, the double salt $SAM^+.HSO_4^-.H_2SO_4.2\ CH_3C_6H_4SO_3H$ separates in the subsequent precipitation stage (f).

If however a volume of methanol equal to at least double the necessary volume is used in stage (e), the double salt $SAM^+.HSO_4^-.H_2SO_4.CH_3C_6H_4SO_3H$ separates in the subsequent precipitation stage (f).

The use of intermediate quantities of methanol leads to the formation of mixtures of the two salts.

The final precipitation of one or other of the new salts according to the invention (stage f) requires the use of an organic solvent chosen from the group consisting of methanol, ether, chloroform, n-propanol, isopropanol, n-butanol, isobutanol, secondary butyl alcohol, isoamyl alcohol and tetrahydrofuran.

The double salts of SAM obtained according to the present invention can be preserved indefinitely in the dry state, as stated, practically unaltered.

The following examples illustrate the method of preparation of the new salts according to the invention, it being however understood that these examples are purely illustrative and do not limit the invention.

The process discovered by us does not require temperatures higher than ambient temperature in any stage, and is carried out in an acid environment. This is very important in avoiding the decomposition of the SAM. Furthermore it does not require complicated and laborious processes such as chromatography over columns of ion exchange resin or carbon, which would make it difficult to carry out industrially.

EXAMPLE 1

To 90 kg of yeast enriched in SAM (6.88 g/kg) in accordance with Schlenk (Enzymologia 29, 283 (1965)) are added 11 l of ethyl acetate and 11 l of water at ambient temperature. After energetic agitation for 30 minutes, 50 l of 0.35 N sulphuric acid are added, continuing agitation for a further hour and a half. After filtering and washing with water, 140 l of solution are obtained containing 4.40 g/l of SAM, equal to 99.5% of that present in the starting material.

A solution of 2.3 kg of picrolonic acid in 24 liters of methylethylketone is added to the previous solution under agitation. After standing for one night, the precipitate is separated by centrifuging and washed with water.

The solid thus obtained is added under agitation to a mixture of 18 liters of a 0.1 N solution of sulphuric acid and p-toluenesulphonic acid, and 18 liters of methylethylketone. After standing, the organic phase separates and is fed to the picrolonic acid recovery system, the aqueous phase is treated with a little methylethylketone to eliminate residual traces of picrolonic acid, decolouring charcoal is added and it is then filtered.

This solution (16.5 l) contains 33.8 g/l of SAM, equal to 90% of the compound present in the yeast. When analysed by thin layer chromatography in accordance with Anal. Biochem. 4, 16–28 (1971) it is known to contain only SAM without traces of its decomposition products or other organic bases.

The above solution is poured into 100 liters of acetone under agitation.

After standing, it is decanted from the solvent and the solid is dissolved in 3.3 kg of a 15% solution of p-toluenesulphonic acid in methanol. After adding decolouring charcoal, the mixture is filtered and added to 25 l of ethyl ether.

1184 g of a well crystalline salt precipitate which is easily filterable, not very hygroscopic, and very soluble in water (more than 20%) with the formation of a colourless solution. The salt is only slightly soluble in methanol and ethanol, and insoluble in acetone, methylethylketone, chloroform, higher alcohols and benzene. From thin layer chromatography in accordance with Anal. Biochem. 4, 16–28 (1971) the product is shown to be free from any impurity.

Centesimal analysis of the salt gave the following results: C = 36.39%, H = 4.6%, S = 16.7%, N = 8.8%; The calculated values for $C_{29}H_{42}N_6R_{19}S_5$ (M.W. 938.98) are: C = 37.09%, H = 4.51%, S = 17.7%, N = 8.95%.

| Moreover: | $H_2SO_4$ | = 20.5% |
|---|---|---|
| | P-toluensulphonic acid | = 36.0% |
| | SAM | = 41.7% |
| Calculated: | $H_2SO_4$ | = 20.89% |
| | P-toluensulphonic acid | = 36.67% |
| | SAM | = 41.54% |

Humidity determined in accordance with K. Fischer: 1.7–2%

The U.V. spectrum of the new compound shows an absorption maximum at 260 nm, $E_1^{\%}{}_{cm} = 182$.

This data agrees with a compound of formula

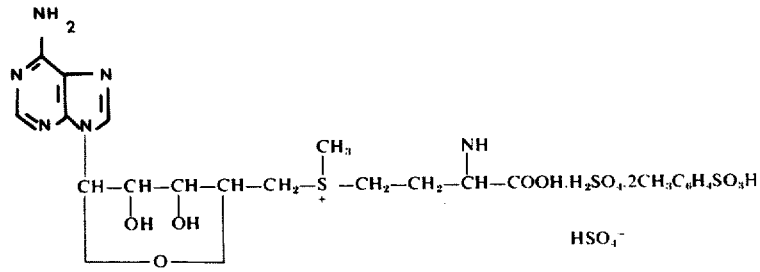

The new compound has further been identified by the enzymatic method based on the enzymatic methylation of nicotine amide or guanidine acetic acid with SAM (G. L. Cantoni, J. Biol. Chem., 189, 745 (1951); G. De La Hoba, B. A. Jamieson, S. H. Mudd and H. H. Richards, J. Amer. Chem. Soc. 81, 3975 (1959).

EXAMPLE 2

1.15 kg of picrolonic acid dissolved in 10 liters of isobutyl alcohol are added to 70 liters of solution originating from the lysis of yeast cells, obtained by using the same raw material and same method as example 1.

After standing for one night, the precipitate formed is separated by centrifuging.

The separated solid is treated with 9 liters of a 0.1 N solution of sulphuric acid and p-toluenesulphonic acid, and with 9 liters of methylisobutylketone.

After standing, the organic phase is separated, while the aqueous phase is freed from traces of picrolonic acid by washing with a little methylisobutylketone. Decolouring charcoal is added and the mixture is filtered, pouring the filtrate into 70 liters of methyl alcohol. After standing, the solid formed is decanted from the solvent and is dissolved in a 15% solution of p-toluenesulphonic acid in methanol (1.65 kg).

After decolouring with charcoal, the filtrate is added to 10 liters of chloroform to obtain an easily filterable crystalline precipitate of SAM disulphase di-p-toluenesulphonate.

The product obtained (1110 g) gave on analysis results which were identical to the product of example 1.

EXAMPLE 3

1.15 kg of picrolonic acid dissolved in 12 liters of n-butanol are added to 70 liters of solution originating from the lysis of yeast cells, obtained by the same lysis method and with the same raw material as example 1. After standing for 1 night, the precipitate is separated by centrifuging.

The solid obtained is divided between 9 liters of a 0.1 N solution of sulphuric acid and p-toluenesulphonic acid, and 12 liters of n-butanol.

After standing, the organic phase separates, while the aqueous phase is freed traces of picrolonic acid by washing with a little n-butanol.

Decolouring charcoal is then added and the mixture is filtered, pouring the filtrate into 65 liters of n-propyl alcohol. After standing, the precipitated solid is decanted from the solvent and dissolved in a 15% solution of p-toluenesulphonic acid in methanol (1.65 kg).

After decolouring with charcoal, the filtrate is poured into 14 liters of n-butanol to obtain a well filterable crystalline precipitate of SAM disulphate di-p-toluenesulphonate.

The final product (1155 g) gave the same results on analysis as the product of example 1.

EXAMPLE 4

Purification of the specific enzyme 50 ml of Sepharose (polysaccharide produced by Pharmacia Fine Chemicals AB, Uppsala — Sweden) caked and suspended in water, are treated with cyanogen bromide in accordance with the known methods for bonding substances containing amine groups to matrices consisting of polysaccharide gel.

An excess of L-lysine is added to the gel so prepared. It is repeatedly washed after the reaction with distilled water, with a pH 8.5 buffer mixture and with a pH 4.5 buffer mixture. The gel is then used for packing a column having a diameter of 1.5 cm and a height of 30 cm. A buffer mixture of 0.05 M triethanolamine and 0.01 M $H_2SO_4$ of pH 8.0 is passed through the column until complete equilibration is obtained.

2 ml of yeast extract containing the specific enzyme are laid on the column, obtained by sonification or by homogenising with dry ice and possibly after enrichment with the specific enzyme. The column is then eluted with the same buffer mixture as used for equilibration, following the distribution of the proteins in the eluate by ultraviolet spectrophotometric measurements. Simultaneously the synthetasis activity is measured in the various fractions in accordance with J. A. Stekol, Methods in Enzymology, vol. 6, pag. 566 (1963). Those fractions displaying a relevant synthesis activity are added together and the solution so obtained shows a specific activity at least 20 times greater than the raw extract. The enzyme can be further concentrated in this solution by precipitation with salts, with organic solvents or in accordance with other known methods for concentrating protein solutions.

Preparation of SAM 30 ml of caked Sepharose gel are activated with cyanogen bromide or by any other known method for bonding proteins to polysaccharide gel matrices.

4 ml of a solution of the specific enzyme purified as above and containing about 100 mg of protein are added to the activated gel. The suspension of activated gel and the enzyme solution are agitated at 4°C for 18 hours.

The resin is washed with water. This wash liquid contains about 70% of the total enzymatic activity initially present in the solution of the specific enzyme. By incubating the Sepharose prepared as above with the aforementioned method for determining synthetasis activity, it is observed that approximately 20% of the total activity is bonded to the polysaccharide.

The Sepharose prepared as above is used for packing a column having a diameter of 1.5 cm and a height of 20 cm. A solution containing 0.675 M triethanolamine, 0.150 M magnesium sulphate, 0.05 M ATP, 0.05 M M-methionine, and 0.01 M KCl is passed through the column at a speed of 5 ml per hour and at a temperature of 25°–27°.

The eluate from the column analysed for SAM content shows that the conversion yield is 30%.

Preparation of double salts of SAM with sulphuric acid and p-toluenesulphonic acid 103 ml of eluate containing 6 g/l of SAM are acidified with $H_2SO_4$ until a pH of 3 is reached, and to this is added under agitation a solution of 2.3 g of picrolonic acid in 25 ml of methylethylketone. After standing for one night, the precipitate is filtered and washed with water. The precipitate is redissolved in 18 ml of a 0.1 N solution of $H_2SO_4$ and p-toluenesulphonic acid, and in 18 ml of methylethylketone.

After agitation and standing, the organic layer is separated and the aqueous layer is treated with a little methylethylketone to eliminate the last traces of picrolonic acid. After separating the water layer, decolouring charcoal is added and the mixture is filtered. 16.5 ml of aqueous colourless solution are obtained, which contains 33.8 g/l of SAM equal therefore to 90% of the SAM contained in the original solution. On thin layer chromatography analysis, the solution is shown to contain only SAM. 16.5 ml of the solution are poured into 100 ml of acetone. After agitation and standing, the liquid is separated by decanting. The solid is dissolved in 6.6 g of a 15% solution of p-toluenesulphonic acid in methanol. After adding decolouring charcoal and filtering, the solution is poured into 25 ml of ethyl ether. It is filtered after standing, and the well crystalline salt obtained weights 0.967 g and has the composition:

$SAM^+.HSO_4^-.H_2SO_4.CH_3C_6H_4SO_3H$. On analysis: calculated for $C_{22}H_{34}O_{16}N_6S_4$: C: 34.46%, H: 4.47%, N: 10.96%, S: 16.72%; found: C: 33.68%, H: 4.65%, N: 10.8%, S: 16.5%; $SAM^+$: 50.5%, $H_2O$: 2.1%, $H_2SO_4$: 25.3%, p-toluenesulphonic acid: 21.7%.

The ultraviolet spectrum shows a maximum at 260 nm, $E_1^{1\%}{}_{cm} = 179$. On repeating the process in an identical manner, but using 3.3 g of a 15% solution of p-toluenesulphonic acid in methanol, in the subsequent precipitation stage using 25 ml of ethyl ether, 1.18 g of the salt $SAM^+.H_2SO_4.2CH_3C_6H_4SO_3H$ is obtained having identical characteristics with those indicated for the product of example 1.

For some years it has been known from biochemical research that SAM is the only specific donot of methyls in living organisms for the biochemical reactions of transfer of the $CH_3$ group, which are fundamental reactions in the lipidic, protidic and glucidic metabolism.

By way of example we give below some of the most important SAM-dependent transmethylation reactions:
- a. N-transmethylation: adenine, carnitine, carnosine, creatine, 2,6-diaminopurine, adrenaline, guanine, hordenine, N'-nicotinamide, phosphatidilcoline, ricinine;
- b. O-transmethylation: N-acetylserotonine, dopamine, epinine, d-adrenaline, 1-adrenaline, ergosterol, 1-noradrenaline, pectine, ubiquinone;
- c. S-transmethylation: 2,3-dimercaptopropanol, $H_2S$, methionine, methylmercaptan, S-mercaptopropionic acid, S-mercaptoethanol, thiopyrimidine, thiouracyl;
- d. C-transmethylation: cytosine, thymine.

This means, referring in particular to the human organism, that SAM acts in the following metabolic processes:

Biosynthesis of choline; biosynthesis of phosphatidylcoline; activity of enzymes which require SH groups; metabolism of catecholamines; metabolism of biogene centroencephalic amines; metabolism of serotonine; metabolism of histamine; metabolism of vitamin B12 and of pholic acid; metabolism of creatine; metabolism of myosine; metabolism of histones; metabolism of RNA; metabolism of DNA; metabolism of protein substances; metabolism of some hormones of cyclopentane perhydrophenantrenic nucleus, the main ones of which are the estrogens; metabolism of the triglycerides.

It has also been known for some time that SAM, once demethylated by the methyltransferasic enzymes, is transformed into S-adenosilhomocysteine (SAO) which is an indirect donor of hydrosulphide groups and hence has a determining importance in the metabolism of all compounds which require SH groups for carrying out their biological activity.

Particularly important among these are some thioenzymes and the sulphurated amino acids.

SAO in its turn is decarboxylated in the organism, and the decarboxylated product is the principal donor of the aminopropyl group, indispensible — according to the most recent biochemical knowledge — for the biosynthesis of polyamines. The process is catalysed by various enzymes among which a specific one is aminopropyl-transferasis.

Summarizing we may say that it is known that SAM in the human organism is closely connected with all biochemical reactions of:
- A. transmethylation (specific yielding of the $CH_3$ group)
- B. transsulphuration (specific yielding of the SH group)
- C. transaminopropylation (specific yielding of the aminopropyl group).

The sum of this knowledge could lead one to think that SAM could have some therapeutic action in the treatment of pathological states linked with the shortage or other deficiency conditions in the organism with respect to some of the many products mentioned above.

However the extreme instability of SAM and the lack, up to the present time, of any method for making it stable for sufficient times under normal ambient conditions has prevented this product from being given any pharmacological or clinical tests and hence has prevented any practical use being found for it in the field of human therapy.

Only after the preparation of the new SAM salts according to the present invention, salts which are practically indefinitely stable at ambient temperature, has it been possible to carry out a systematic pharmacological and clinical study which has led to the discovery for the new salts of therapeutic properties completely surprising in their quality and intensity.

From the enormous quantity of pharmacological and clinical data collected for this new product, we give hereinafter only some elements sufficient to clearly indicate to experts in the art the essential characteristics of the new product and its main uses in human therapy.

For simplicity hereinafter we shall indicate simply by "SAM salt" the two double salts according to the invention, because of their absolute identical use.

In the pharmacological and clinical data we indicate for the sake of simplicity with the abbreviation SAM the salt
Also the administered amounts are always of
$SAM^+.HSO_4^-.H_2SO_4.2CH_3C_6H_4SO_3H$.
However the data may refer equally well to the other double salt.

TOXICITY — the SAM salt according to the invention has proved absolutely free from acute toxicity, chronic toxicity, local intolerance or secondary effects.

In particular, the $DL_{50}$ in the mouse is greater than 6 g/kg/os and 2.5 g/kg/i.p.

The tolerability and chronic toxicity tests were carried out on rats of the Wistar and Sprague-Dowley stock administering for 12 months 10–20 mg/kg per day of product: at the end of the treatment the various organs and apparatus showed no pathological alteration.

The tetratogenesis tests were carried out on rabbits and rats: even with the administration of massive doses of SAM, approximately 10 times the maximum therapeutical doses, no tetratogenic actions were encountered or any malformations in the embryons or terminal feti.

The addition of doses up to 0.1–0.2 mg/ml of product in surviving cultures of human lymphocytes or hepatic mouse cells does not product any change in the blasticising index for the cellular elements.

The intravenous administration of doses up to 40 mg/kg does not produce any pyrogenic manifestation in the rabbit.

The venous administration in the rabbit and cat of 40 mg/kg doses does not cause any change in the carotid pressure, the cardiac and respiratory frequency or the electrocardiac trace.

The local tolerability of the intermuscular injection, even after administrations repeated over 180 days, and of the intravenous injection in the marginal vein of the auricular pavillon of the rabbit, is excellent.

In man, in young volunteer healthy subjectes of both sexes subjected to administration by the rapid intravenous method or by phleboclysis of doses of SAM equal to 10–300 mg/ (average weight 70 kg), the simultaneous examination of the minimum and maximum pressure and of the pulse and respiratory frequency at 1,5,15,20,30,60 minutes and at 2,3,6,8,10,12,24 hours from the end of administration does not show any variation from normal values.

The electrocardiograph trace does not show any variations in the PQ interval, in the ST section, nor any appearance of extrasistol or other alterations at 30'', 1', 2', 3', 5', 10' and 20' from administration.

In the hemopoietic apparatus and in the hepatic and renal operation there were no variations which were statistically significant from normal.

PHARMACOLOGY

We would repeat here that each time we speak hereinafter of the administration of SAM, we mean that the following has been administered:
SAM$^+$.HSO$_4^-$.H$_2$SO$_4$.2 CH$_3$C$_6$H$_4$SO$_3$H and/or SAM$^+$.HSO$_4^-$.H$_2$SO$_4$.CH$_3$C$_6$H$_4$SO$_3$H. In order to indicatively determine how SAM is distributed in the tissues, S-Adenosilmethionine (Methyl C$^{14}$) was prepared. The distribution of this product in rats was studied by administering a dose of 10 mg/kg/e.v. equal to 24 μci of radioactive product. The specific activity of the product was 58 mCi/m moles. Parallel to this, an autoradiographic study was made on the mouse. The results of these two experiences show that SAM is distributed very rapidly to all the tissues.

We give by wey of example a part of the data relative to each of the organs considered:
Distribution of SAM in some rat tissues.
The values are expressed as μgr/gr.

| Tissue | 15' | 1 h | 4 h | 8 h | 24 h |
|---|---|---|---|---|---|
| Liver | 4.02 | 7.47 | 13.1 | 13.4 | 13.5 |
| Suprarenal glands | 4.26 | 8.46 | 11.7 | 10.8 | 10.9 |
| Spleen | 3.15 | 2.96 | 8.1 | 6.2 | 6.7 |
| Hypophysis | 5.6 | 5.8 | 19.5 | 11.3 | 10.3 |
| Hypothalamus | 0.7 | 1.5 | 2.4 | 3.0 | 3.2 |
| Rind | 0.6 | 1.1 | 1.8 | 2.1 | 2.3 |
| Plasma | 18.6 | 5.2 | 5.3 | 4.5 | 3.1 |

It was consequently deduced that the new salts according to the present invention donate the CH$_3$ group to all the tissues provided with methyltransferasis activity. In other words the capacity of the new products according to the invention to electively localise themselves in all the organs provided with methyltransferasis systems was deduced.

This was confirmed by successive pharmacological tests. A whole series of tests carried out on rats has shown that the new compounds exercise a considerable protective and resolutive action in hepatic steatosis by hyperlipidic-hyperproteic diet according to Handler, in steatosis by acute alcoholic intoxication and by other toxic agents (carbon tetrachloride, bromobenzene etc.) by the administration of only 15 mg/kg/i.p.; both from the morphohistochemical and analytical point of view, the SAM significantly reduced the accumulation of lipids at the hepatocite level while it favours the restoration of normal levels of phospholipids reduced after intoxication with CCl$_4$.

Hepatic phospholipids in rats after intoxication with CCl$_4$ and treatment with SAM.

| Treatment | Total phospholipids (mg/g) |
|---|---|
| Physiological solution | 30.57 ± 1.18 |
| CCl$_4$ | 18.87 ± 1.06 |
| CCl$_4$ + SAM 15 mg/kg/i.p. | 27.20 ± 1.25 |
| CCl$_4$ + SAM 150 mg/kg/i.p. | 20.87 ± 0.42 |
| CCl$_4$ + Ad-Met 15 mg/kg/i.p. | 19.9 ± 0.92 |

The values are the average ± E.S. of 10 values for each group.

In studying the hepatoprotective activity we have used an experimental device which produces in the rat the so-called hepatic cholesterol degeneration (Ridout and Coll., Biochem. J. 52, 99, 1952).

In this method, by means of a suitable diet, a conspicuous increase in the total hepatic fats and hepatic cholesterol are obtained in the animals. The substances which act in the lipidic metabolism reduce or annul this increase.

The animals were divided into six groups. The first group was administered with a diet which was varied at will. The second group was administered with the basic diet of Ridout (20 g per rat per day); the other groups were administered with the same diet in the same doses but enriched with cholesterol to the extent of 0.2 g/rat/day. The treatment lasted 3 weeks.

The groups 4,5,6 were administered with SAM in the following doses: 1,2,5 mg/kg/i.p. per day.

At the end of 3 weeks all the animals were killed, the livers were withdrawn and the total fats (Best and Coll., Biochem. J. 40, 368, 1966) and cholesterol (Sperry and Brand, J. Biol. Chem. 150, 315, 1943) were determined.

The results showed that the batches subjected to treatment with SAM in doses of 1–2 mg/kg/i.p. were poorly protected, while the batch treated with 5 mg/kg/i.e. was completely protected.

Hepatic cholesterol and total fats at the end of the experiment (average per batch)

| Batch | Fresh liver weight g | Total fats g | Total fats % | Cholesterol mg | Cholesterol % |
|---|---|---|---|---|---|
| I | 15 | 1.41 | 9.4 | 40 | 2.6 |
| II | 18 | 1.93 | 10.6 | 68 | 3.7 |
| III | 16 | 3.84 | 24.0 | 92 | 5.7 |
| IV | 17 | 3.70 | 21.6 | 90 | 5.2 |
| V | 16 | 3.5 | 21.9 | 67 | 4.1 |
| VI | 16 | 2.0 | 12.5 | 61 | 3.8 |

Another pharmacological aspect investigated by us was the antiinflammatory and analgesic effects of SAM.

Ot the various tests we shall mention the most classic, namely the edema by carragenine and by egg white as a test for acute inflammation; and granuloma by cotton peelets and arthritis by adjuvant as a test for chronic inflammation. In all cases SAM proved active both administered orally (dose between 20 and 100 mg/kg) and parenterally (doses between 10 and 20 mg/kg) in comparison with other known pharmaceutical products (Ibuprofen-Indometacina). The analgesia tests were in the form of the hot plate tests and stretching by acetic acid, and the Randal and Drlitto tests in the rat. The pharmaceutical product also proved active in these tests in comparison with known pharmaceutical products studied.

A further aspect considered by us was the possible action of SAM on the sleeping time by barbiturates.

For this purpose an experiment was made in which groups of mice received hexobarbital in a dose of 80 mg/kg/i.p. in accordance with the method of Holten and Larsen (Acta Pharmacol. Toxicol. 1956, 12, 346); one group was the control group and the second received SAM in a dose of 10 mg/kg/i.p. (table).

|  | Sleeping time (min.) |
|---|---|
| Controls | 24.4 ± 2.7 |
| SAM 10 mg/kg/i.p. | 41.2 ± 5.8 |

An examination of the data showed that SAM is active in prolonging the sleeping time induced by hexobarbital.

CLINICAL TESTS

Where the administration of SAM is mentioned hereinafter, this signifies the administration of $SAM^+.HSO_4^-.H_2SO_4.2CH_3C_6H_4SO_3H$ and/or $SAM^+.HSO_4^-.H_2SO_4CH_3C_6H_4SO_3H$.

Following the information gained from the pharmacological tests, the clinical tests were orientated on morbid affections in which the following appear primitively or secondarily altered:

1 — the metabolism of lipids
2 — the metabolism of protids and glucids
3 — the metabolism of catecholamines and the biogene amines.

1. From tests conducted clinically on hundreds of subjects using doses of SAM varying over a very wide interval, it was found that the new compound induces a rapid fall in the hepatic lipids in the hepatosteatosis of the most varied pathogenesis, identifiable by a bioptic examination repeated after the end of the treatment cycle, even after 60 days from the end of treatment. The administration of the product also induces a marked fall in the high values of total cholesterolemia, of hypertriglyceridemia and normalises the altered $\beta/\alpha$ lipoproteic ratios in subjects with hyperdislipidemia in the uncompensated stage.

This hypocholesterolemising and hypolipemising action is verified even in doses of about 20–30 mg administered 2–3 times per day, and is proportional to the dose.

In clear arteriosclerosis with clinical manifestations of the psychoaffective sphere, with turbemnesics and secondary centroencephalics (determination by arteriosclerotic encephalopathia) and phenomena of cerabral hypoxia, the administration of SAM by intramuscular or, in graver cases, by intravenous injection or by low phleboclysis, in doses between 20 and 40 mg 3–4 times per day, has shown a very favourable modification of the sumptomatology.

In particular, in clear hypoxydotic states the recovery of the functions related to the like of relationship was very quick and statistically significant.

In post-apoplectic syndromes a greater rapidity was found in the improvement of the clinical framework.

2. Hundreds of subjects were treated clinically affected with: secondary hypoprotidemias and disprotidemias; persistent and aggressive cronic hepatopathias; precyrrotic and cyrrotic states; malabsorption syndromes, protide dispersing syndromes. The administration of doses variable between 20 and 200 mg of SAM per day by intermuscular or intravenous injection or orally, according to the gravity of the case, caused a statistically significant increase in the total protidemia, an increase in the albumin amount and a tendency to normalise the altered percentage ratios between the electrophoretic fractions of the serum. This protein anabolising activity was followed by an often very important improvement in the subjective symptomology and the general objective conditions, and by the normalizing of all the tests of hepatic functionality.

3. Particularly surprising results were obtained in clinical applications of the new enzymatic salt according to the invention, in which morbid frameworks existed which were clearly correlated with modifications in the exchange of biogene amines, for example:

a. pathological frameworks of neuropsychiatric pertinence;
b. Parkinsons disease and Parkinsonism of various eziopathogeneses;
c. Antiphologistic and analgesic action in the treatment of osteo arthritis, and antalgic activity in certain neurological manifestations;
d. Disturbances of the sleeping-waking rhythm.

With regard to point (a), a vast clinical casuistry conducted by examining the clinical behaviour and the tests of Hamilton and Wittenberg, has clearly shown that the administration of doses varying between 20 and 50 mg of SAM 3–4 times per day for a period of 5–15 days induces, excluding any other form of therapy, a significant remission of the main parameters considered for the diagnosis of depressive forms.

With regard to point (b) relative to the treatment for Parkinsons disease and Parkinsonisms, it has been found that:

The administration of SAM in doses of 10–40 mg per day by intramuscular or intravenous injection, or orally — according to the gravity of the case — in association with the habitual therapy with Levodopa, gives rise to a statistically more significant improvement in the akinesia and rigidity with respect to that which occurs in patients treated only with Levodopa. favourable modifications are also found in the extent of the Parkinson tremor, which cannot be modified by Levodopa alone.

The administration of SAM distinctly improves the Levodopa-dependent psychic disturbances, with particular regard to depressive states and psychic manifestations of irritative type.

The administration of SAM in the aforementioned doses significantly blocks the train of Levodopa side effects of the various organs and apparatus, with particular regard to neusea, vomit, inappetite, hypotension, asthenia, cephalea, hypersudoration and insomina.

With regard to point (c), SAM, which pharmacological results show to have intense antiphlogistic and analgesic activity, has proved active in all osteoarthritic forms treated with a dose of 30 mg twice a day by intermuscular or intravenous injection, and 30–50 mg orally 4 times per day.

After only 7 days of treatment, the muscular spasm, the limitation of movement, localised pain, and rigidity were influenced in a statistically significant manner, with respect to the placebo. No case of gastric pyrosis was observed in 90 cases treated. The search for concealed blood in the feces never showed any modification during the treatment.

SAM, compared with a non-steroid antiphlogistic drug commonly used in a double blind study, proved to possess a therapeutic efficiency equal to indomethacin.

The antalgic activity of SAM was also tested in different subjects with different neurological frameworks: neuritis, polyneuritis, anthralgia, sciatica, radiocolitis, torticollis. The therapeutic effect was available and efficient from the first day of administration of a dose of 15 mg twice a day by intermuscular injection or 30–50 mg 3–4 times per day orally. Analogous results were obtained in subjects with recurring and resistant cephalalgia with the administration of the drug orally in masticable tablets.

With regard to point (c), i.e. disturbances of the sleeping-waking rhythm, with particular regard to insomnia, the new product according to the invention is able with a dose of 10–30 mg orally, to considerably improve the altered sleeping-waking ratios by inducing a physiological sleep without recurrence to the use of barbiturates or other substances of cortical and centroencephalic depressive action.

From that summarized heretofore the numerous unexpected perspectives opened up by the new drug in the field of human therapy are evident.

Summarizing, we can say that the fields of use already ascertained are:

treatment of hepatopias, hyperdislipidemias, generalised or local arteriosclerosis, psychiatric manifestations of depressive and neurological type, degenerative arthromathies, neurological algic manifestations and disturbances of the sleeping-waking rhythm, whereas many other fields of use still remain to be examined and ascertained.

The new SAM salts are preferably administered by intramuscular or intravenous injection, or in oral or sublingual tablets, or in capsules.

Some pharmaceutical compositions are given below:

```
a) A 400 mg tablet contains
   SAM salt                           66.66 mg
   Excipients:
   Starch
   Lactose
   Magnesium stearate
   Talc
   Aroma                              q.n. 400 mg
b) A 250 mg capsule contains
   SAM salt                           66.66 mg
   Excipients:
   Starch
   Lactose
   Magnesium stearate
   Na₃PO₄                             q.n. 250 mg
c) A lyophilised phial contains
   SAM salt                           11.11 mg
   A muscular solvent phial contains
   Lidocaine                          20 mg
   Solution of phosphate buffers      q.n. to 3 ml
d) A lyophilised phial contains
   SAM salt                           33.33 mg
   A muscular solvent phial contains
   Lidocaine                          20 mg
   Solution of phosphate buffers      q.n. to 3 ml
e) A 2 g suppository contains
   SAM salt                           111.11 mg
   Suppository mass                   q.n. to 2.0 g
```

Other forms of administration may be:
a. Drinkable bottles
b. Liquids for ocular instillation
c. Liquids for intranasal instillation
d. Liquids for aerosol or spray application
e. Liquids and ointments for topical use in which the active principle is diluted in the normal acceptable pharmaceutical solvents ("Tecnologia Farmaceutica" — Second Volume, Silvano Casadia — Second Edition — ed. Cisalpino-Goliardica — Milan — 1972).

In conclusion we may say that the therapeutic doses of SAM lie between 5 and 300 mg per day, according to the particular type and gravity of the affection treated.

Larger doses may be used if necessary in view of the absolute absence of toxicity of the salts according to the invention.

What is claimed is:

1. Double salts of S-adenosil-L-methionine (SAM) with sulphuric acid and p-toluenesulphonic acid.

2. Double salt as claimed in claim 1 corresponding to the formula $SAM^+.HSO_4^-.H_2SO_4.2\ CH_3C_6H_4SO_3H$.

3. Double salt as claimed in claim 1 corresponding to the formula $SAM^+.HSO_4^-.H_2SO_4.CH_3C_6H_4SO_3H$.

4. Process for preparing double salts of S-adenosil-L-methionine (SAM) with sulphuric acid and p-toluensulphonic acid in which a. a concentrated solution of SAM is prepared; b. the SAM present in the solution is precipitated by acidifying with a solution of picrolonic acid; c. the SAM picrolonate is dissolved in a mixture consisting of equal parts by volume of an aqueous solution of equal normalities of p-toluenesulphonic acid and sulphuric acid, and an organic solvent partially miscible with water; d. the SAM salt is precipitated from the aqueous layer by a ketone or alcohol based solvent totally soluble in water; e. the precipitated salt is dissolved in a solution of p-toluenesulphonic acid in methanol; f. the double salt of SAM with sulphuric acid and p-toluenesulphonic acid is precipitated by a suitable organic solvent.

5. Process as claimed in claim 4, in which the stage (a) is carried out by the lysis of yeast cells by treatment with ethyl acetate and sulphuric acid at ambient temperature.

6. Process as claimed in claim 4, in which the stage b. is carried out using solutions of picrolonic acid in water or in an organic solvent soluble in water.

7. Process as claimed in claim 4, in which the stage c. is carried out using aqueous solutions of equal normalities of sulphuric acid and p-toluenesulphonic acid, both lying between 0.05 and 0.2.

8. Process as claimed in claim 4, in which the stage d. is carried out using 4–8 volumes, with respect to the aqueous solution, of an organic solvent chosen from the group consisting of acetone, methyl alcohol, ethyl alchol, propyl alcohol.

9. Process as claimed in claim 4, in which the stage e. is carried out using 10–4% solutions of p-tolurnsulphonic acid in methanol.

10. Process as claimed in claim 9, in which the minimum quantity of methanol necessary for dissolving the salt is used.

11. Process as claimed in claim 9 wherein the methanol is used in a volume equal to at least double that necessary to dissolve the precipitate originating from stage d.

12. Process as claimed in claim 10, in which the double salt $SAM^+.HSO_4^-.H_2SO_4.2CH_3C_6H_4SO_3H$ precipitates during treatment with the organic solvent in accordance with stage f.

13. Process as claimed in claim 11, in which the double salt $SAM^+.HSO_4^-.H_2SO_4.CH_3C_6H_4SO_3H$ precipitates during treatment with the organic solvent in accordance with stage f.

* * * * *